United States Patent [19]

Foster

[11] 4,279,828
[45] Jul. 21, 1981

[54] PROCESS FOR SEPARATING 3-HYDROXY STEROIDS OR STEROLS FROM MIXTURES SUCH AS LIPIDS

[75] Inventor: Charles H. Foster, Kingsport, Tenn.

[73] Assignee: Eastman Kodak Company, Rochester, N.Y.

[21] Appl. No.: 159,095

[22] Filed: Jun. 13, 1980

[51] Int. Cl.³ .............................................. C07J 9/00
[52] U.S. Cl. ............................................. 260/397.25
[58] Field of Search ................................... 260/397.25

[56] References Cited

U.S. PATENT DOCUMENTS

| | | | |
|---|---|---|---|
| 4,057,541 | 11/1977 | Weber et al. | 260/397.25 |
| 4,148,810 | 4/1979 | Struve | 260/397.25 |

Primary Examiner—Elbert L. Roberts
Attorney, Agent, or Firm—Clyde L. Tootle; Daniel B. Reece, III

[57] ABSTRACT

A process for separating 3-hydroxy steroids from mixtures of lipids by combining a solution of the sterol-containing mixture in isopropanol or other similar alcoholic solvents with a slurry or solution of calcium dichloride in isopropanol or other similar alcoholic solvents. The complexed sterols are isolated by evaporating the alcoholic solvents, washing the residue with a hydrocarbon solvent and filtration. The sterols can be subsequently liberated from the complex by treatment with an aqueous/alcohol and isolated by filtration.

9 Claims, No Drawings

PROCESS FOR SEPARATING 3-HYDROXY STEROIDS OR STEROLS FROM MIXTURES SUCH AS LIPIDS

The present invention relates to a process for separating sterols from mixtures of such sterols and lipids.

Various processes are known in the art for separating sterols such as 3-hydroxy steroids from mixtures of such sterols and lipids. One such mixture is phytosterols in soybean oil deodorizer distillate. The separation of the 3-hydroxy steroids from such mixtures is important because these 3-hydroxy steroids are useful as raw materials for production of steroid drugs such as hydrocortisone. One such known process in German Pat. No. 827,199 is described wherein the mixture is dissolved, preferably in a hydrocarbon solvent, and is heated with a four- to sixteen-fold excess of anhydrous zinc chloride. After cooling of the solution, the precipitated ZnCl-sterol adduct can be separated out and split into the individual components. Another such known process as set forth in British Pat. No. 1,164,769 describes a method for the isolation of sterols from mixtures wherein the mixture is dissolved, preferably in a hydrocarbon solvent, the solution is mixed with an aqueous solution of a metal salt which is suitable for complex formation, the water is progressively removed by azeotropic distillation, and the precipitated adduct is isolated and split in a conventional manner after cooling of the mixture.

Such known methods have the disadvantage that they are technically very costly on account of the high reaction temperature (customarily over 100° C.) and that in the isolation of many 3-hydroxy steroids and 3-oxo steroids considerable loss of product is experienced, since these steriods are destroyed under these conditions. In addition, these known methods often have the disadvantage that the recovery of the metal salt used for formation of the adduct, which is necessary in a method carried out on large scale simply with regard to environmental considerations, is often very costly.

Another prior art process for separating 3-hydroxysteroids from mixtures of such steroids and lipids as disclosed in U.S. Pat. No. 4,057,541 is carried out by forming a solution of a mixture of one or more 3-hydroxy steroids and lipids in methyl isobutyl ketone or methyl n-amyl ketone, or mixtures thereof, is mixed with calcium bromide or a solution of calcium bromide in methyl isobutyl ketone or methyl n-amyl ketone, or mixture thereof, and the precipitated adduct separated and split in a known manner.

This process however uses the more expensive calcium bromide which is soluble in the ketone solvent. If the less expensive calcium dichloride is used the complexing rates are too slow to be commercially useful due to the insolubility of the calcium dichloride in organic solvents suitale for complex formation. In order to use the less expensive calcium dichloride it has previously been necessary to use a mixture of a protic and aprotic solvent as disclosed in U.S. Pat. No. 4,148,810. The process using two different solvents is undesirable due to the cost of recovery of the two solvents. It would therefore be a significant advance in the state of the art to provide a relatively simpler, less expensive and less energy and labor consuming process useful commercially to separate 3-hydroxy steroids from mixtures of such sterols and lipids.

In accordance with the present invention, a process is provided for isolating 3-hydroxy steroids from such sterols and lipids by merely combining a solution of the sterol-containing mixture in a suitable alchoholic solvent with a slurry or solution of calcium dichloride in a suitable alcoholic solvent. The resulting mixture can then be stirred or agitated at ambient temperature for a suitable period to form the sterol-$CaCl_2$ complex. The alcoholic solvent is then removed and the residue washed with an aliphatic solvent and the sterol-$CaCl_2$ complex isolated by filtration. The sterols are liberated from the sterol-$CaCl_2$ complex by treatment with an aqueous alcoholic wash and isolated by filtration.

The alcoholic solvents useful in the present invention are aliphatic alcohols such as methanol, ethanol, propanol, isopropanol, butanol and the like. The amount of alcohol used depends on the solubility of the sterol-lipid concentrate. The amount of calcium dichloride used depends on the concentration of the sterols in the sterol-lipid concentrate. The greater the amount of sterol present, the greater the amount calcium dichloride necessary to provide sufficient $CaCl_2$ to form complexes with the sterols.

The hydrocarbon solvent used to wash the residue obtained after removal of the alcoholic solvent can be any suitable solvent which does not dissolve the complex. Such solvents include heptane, hexane, toluene, cyclohexane, methyl ethyl ketone, methyl isobutyl ketone and the like.

The alcoholic solvent can be removed after the formation of the sterol-$CaCl_2$ complex preferably by evaporation under vacuum.

It should be noted that heat may be used to dissolve the sterol-lipid concentrate in the suitable alcoholic solvent and during complex formation, but is not necessary.

This invention can be further illustrated by the following examples, although it will be understood that these examples are included merely for purposes of illustration and are not intended to limit the scope of the invention unless otherwise specifically indicated.

EXAMPLE 1

A solution of 100 g of soy sterol concentrate (60% sterols) in 900 ml isopropyl alcohol was treated with a mixture of $CaCl_2$ (10.0 g) in 100 ml of isopropanol. The resulting mixture was stirred one hour at room temperature, then the solvent was evaporated under vacuum. The residue was washed with cyclohexane and isolated by filtration. Sterols (37 g) were liberated from the complex by treatment with $H_2O$/isopropanol (10/1) and isolated by filtration (assay, 100% sterols, 24% stigmasterol).

The process of the present invention provides an improved process for separating 3-hydroxy steroids from mixtures of such sterols and lipids. Further, the 3-hydroxy steroids can be used to provide starting materials for preparation of valuable steroids.

The invention has been described in detail with particular reference to preferred embodiments thereof, but it will be understood that variations and modifications can be effected within the spirit and scope of the invention.

I claim:

1. A process for separating 3-hydroxy steroids from sterol-lipid containing mixtures comprising combining a solution of the sterol-containing mixture in an aliphatic solvent with a slurry or solution of $CaCl_2$ in an aliphatic solvent and agitating said combined solutions for a sufficient time to provide sterol -$CaCl_2$ complexes, removing said aliphatic solvent, washing said residue with a hydrocarbon solvent and recovering said sterol -$CaCl_2$ complex.

2. A process according to claim 1 wherein said alcoholic solvent is removed by distillation.

3. A process according to claim 2 wherein said alcoholic solvent is isopropanol.

4. A process according to claim 3 wherein said washing is carried out with cyclohexane.

5. A process according to claim 3 wherein said washing is carried out with methylethyl ketone.

6. A process according to claim 3 wherein said washing is carried out with methylisobutyl ketone.

7. A process according to claim 3 wherein said washing is carried out with heptane.

8. A process according to claim 3 wherein said washing is carried out with hexane.

9. A process according to claim 3 wherein said washing is carried out with toluene.

* * * * *